United States Patent
Anderson

(10) Patent No.: US 8,814,867 B2
(45) Date of Patent: Aug. 26, 2014

(54) PERCUTANEOUS TECHNIQUE AND IMPLANT FOR EXPANDING THE SPINAL CANAL

(75) Inventor: D. Greg Anderson, Moorestown, NJ (US)

(73) Assignee: Innovative Surgical Designs, Inc., Bloomington, IN (US)

( * ) Notice: Subject to any disclaimer, the term of this patent is extended or adjusted under 35 U.S.C. 154(b) by 0 days.

(21) Appl. No.: 13/448,597

(22) Filed: Apr. 17, 2012

(65) Prior Publication Data

US 2012/0215312 A1   Aug. 23, 2012

Related U.S. Application Data

(60) Division of application No. 12/755,569, filed on Apr. 7, 2010, now Pat. No. 8,157,847, which is a continuation of application No. 11/656,790, filed on Jan. 22, 2007, now abandoned, which is a continuation of application No. 10/102,525, filed on Mar. 19, 2002, now Pat. No. 7,166,107, which is a continuation-in-part of application No. 09/659,180, filed on Sep. 11, 2000, now Pat. No. 6,358,254.

(51) Int. Cl.
*A61B 17/56* (2006.01)
*A61B 17/70* (2006.01)

(52) U.S. Cl.
USPC .................................................... 606/63

(58) Field of Classification Search
USPC ............ 606/246, 63, 301, 313, 315, 317, 90, 606/96, 105; 623/17.11, 17.16; 411/55, 71, 411/80.1, 80.6
See application file for complete search history.

(56) References Cited

U.S. PATENT DOCUMENTS

| | | | |
|---|---|---|---|
| 2,244,683 | A | 6/1941 | Fisher |
| 2,261,230 | A | 11/1941 | Cox et al. |
| 3,174,387 | A | 2/1965 | Fischer |
| 3,896,504 | A | 7/1975 | Fischer |

(Continued)

FOREIGN PATENT DOCUMENTS

| | | |
|---|---|---|
| AU | 516581 | 6/1981 |
| JP | 11004840 | 1/1999 |

(Continued)

OTHER PUBLICATIONS

Patent Abstracts of Japan, vol. 2000; No. 09, Oct. 13, 2000, and JP2000152951, Jun. 6, 2000 (abstract).

(Continued)

*Primary Examiner* — Pedro Philogene
*Assistant Examiner* — David Comstock
(74) *Attorney, Agent, or Firm* — Blank Rome LLP

(57) ABSTRACT

Expanding a spinal canal by drilling a cylindrical passage in each pedicle of a vertebra, making a circumferential pedicle cut (osteotomy) through each pedicle from within the passage, separating each pedicle cut by inserting an implant into the passage to distract the pedicle cut (i.e., lengthen the pedicle) to expand the spinal canal, and securing each pedicle cut, allowing the vertebra to heal with the spinal canal expanded. The implant can include an outer sleeve, an inner bolt, and expandable flanges. The outer sleeve includes an upper and a lower portion, with the expandable flanges therein. Rotation of the inner bolt causes the upper and lower portions of the outer sleeve to separate, causing the pedicle cut to widen and the expandable flanges to radially extend into and stabilize the widened pedicle cut for expansion of the spinal canal.

20 Claims, 14 Drawing Sheets

(56) References Cited

U.S. PATENT DOCUMENTS

| | | |
|---|---|---|
| 4,013,071 A | 3/1977 | Rosenberg |
| 4,716,893 A | 1/1988 | Fischer et al. |
| 4,917,704 A | 4/1990 | Frey et al. |
| 4,955,908 A | 9/1990 | Frey et al. |
| 5,034,011 A | 7/1991 | Howland |
| 5,059,193 A | 10/1991 | Kuslich |
| 5,108,404 A | 4/1992 | Scholten et al. |
| 5,176,678 A | 1/1993 | Tsou |
| 5,258,031 A | 11/1993 | Salib et al. |
| 5,263,803 A | 11/1993 | Anquetin |
| 5,425,772 A | 6/1995 | Brantigan |
| 5,480,440 A | 1/1996 | Kambin |
| 5,489,210 A | 2/1996 | Hanosh |
| 5,496,322 A | 3/1996 | Mathews |
| 5,653,762 A | 8/1997 | Pisharodi |
| 5,653,763 A | 8/1997 | Errico et al. |
| 5,722,977 A | 3/1998 | Wilhemy |
| 5,725,527 A | 3/1998 | Biedermann et al. |
| 5,766,251 A | 6/1998 | Koshino |
| 5,772,663 A | 6/1998 | Whiteside et al. |
| 5,827,285 A | 10/1998 | Bramlet |
| 5,836,948 A | 11/1998 | Zucherman et al. |
| 5,964,761 A | 10/1999 | Kambin |
| 5,980,572 A | 11/1999 | Kim et al. |
| 6,008,433 A | 12/1999 | Stone |
| 6,009,531 A | 12/1999 | Selvidge et al. |
| 6,018,094 A | 1/2000 | Fox |
| 6,077,268 A | 6/2000 | Farris et al. |
| 6,080,157 A | 6/2000 | Cathro et al. |
| 6,099,531 A | 8/2000 | Bonutti |
| 6,129,763 A | 10/2000 | Chauvin et al. |
| 6,224,599 B1 | 5/2001 | Baynham et al. |
| 6,248,106 B1 | 6/2001 | Ferree |
| 6,270,501 B1 | 8/2001 | Freiberg et al. |
| 6,358,254 B1 | 3/2002 | Anderson |
| 6,402,750 B1 | 6/2002 | Atkinson |
| 6,428,256 B2 | 8/2002 | Wieser |
| 6,610,091 B1 | 8/2003 | Reiley |
| 6,635,087 B2 | 10/2003 | Angelucci et al. |
| 7,166,107 B2 | 1/2007 | Anderson |
| 8,157,847 B2 | 4/2012 | Anderson |
| 2003/0028251 A1 | 2/2003 | Mathews |
| 2003/0212400 A1 | 11/2003 | Bloemer et al. |
| 2006/0241774 A1 | 10/2006 | Attali et al. |
| 2007/0219555 A1 | 9/2007 | Anderson |
| 2008/0221623 A1 | 9/2008 | Gooch |
| 2010/0168751 A1 | 7/2010 | Anderson |
| 2010/0198277 A1 | 8/2010 | Anderson |

FOREIGN PATENT DOCUMENTS

| | | |
|---|---|---|
| JP | 2000139970 | 5/2000 |
| JP | 2000152951 | 6/2000 |
| JP | 2001079024 | 3/2001 |
| WO | WO03/079914 | 10/2003 |
| WO | WO97/09940 | 3/2007 |

OTHER PUBLICATIONS

Patent Abstracts of Japan, vol. 2000, No. 08, Oct. 6, 2000, and JP 2000139970, May 23, 2000 (abstract).

Patent Abstracts of Japan, vol. 1999, No. 04, Apr. 30, 1999, and JP11004840, Jan. 12, 1999 (abstract).

International Search Report and Written Opinion; International Application No. PCT/US2009/065869; International Filing Date Nov. 25, 2009; 10 pages.

International Search Report; International Application No. PCT/US03/08565; International Filing Date Mar. 19, 2003; 3 pages.

First Examination in Australia Patent Application No. 2003220421 (now patented); Oct. 17, 2007 and Reply dated Nov. 12, 2008; 4 pages.

International Preliminary Report on Patentability. International Application No. PCT/US2003/008565; dated Mar. 2, 2010; 3 pages.

International Preliminary Report on Patentability; International Application No. PCT/US2009/065869; dated May 31, 2011; 9 pages.

PERCUTANEOUS TECHNIQUE AND IMPLANT FOR EXPANDING THE SPINAL CANAL

RELATED INVENTIONS

This application is a division of U.S. application Ser. No. 12/755,569, filed Apr. 7, 2010 (now U.S. Pat. No. 8,157,847); which application is a continuation of U.S. application Ser. No. 11/656,790, filed Jan. 22, 2007; which application is a continuation of U.S. application Ser. No. 10/102,525, filed Mar. 19, 2002 (now U.S. Pat. No. 7,166,107); which application is a continuation-in-part of U.S. application Ser. No. 09/659,180, filed Sep. 11, 2000 (now U.S. Pat. No. 6,358,254). The above-identified related applications are incorporated herein by reference.

FIELD OF THE INVENTION

The present invention relates generally to spinal surgery, and more particularly to a method and apparatus for expanding a spinal canal to relieve pressure on spinal nerves.

BACKGROUND OF THE INVENTION

Spinal Stenosis, or narrowing of the spinal canal, inflicts millions of people with back and leg pain due to compression of spinal nerves. Severe spinal stenosis often leads to surgery in an effort to relieve compressed nerves and lessen back and leg pain. Spinal laminectomy is the traditional operation performed to treat spinal stenosis. In the spinal laminectomy, posterior aspects of the spinal column are removed to "unroof" the spinal canal to relieve the pressure on the nerves. Specifically, a spinous process, larnina and portions of various facet joints are the posterior aspects of the spinal column surgically excised.

Although the spinal laminectomy is often successful in relieving pressure on the nerves of the spinal canal, several problems and disadvantages arise as a result of the laminectomy. First, the laminectomy removes important sites of back muscle attachment leading to back muscle dysfunction and pain. Second, the laminectomy exposes the nerve sac causing scar tissue to form around the nerves. Scar tissue may prevent normal motion of the nerves, leading to recurrent pain. Third, the laminectomy can destabilize the spine resulting in a forward slippage of one vertebra on another. Vertebral slippage can cause recurrent pain and deformity. Fourth, the laminectomy requires a large surgical exposure and significant blood loss, making the laminectomy dangerous for older patients. Finally, spinal stenosis can recur following the laminectomy, requiring risky revision surgery.

Laminectomy risks have led surgeons to seek an alternative for patients with severe spinal stenosis. Some surgeons choose to treat spinal stenosis with multiple laminotomies. Laminotomies involve removing bone and soft tissue from the posterior aspect of the spine making "windows" into the spinal canal over areas of nerve compression. Multiple laminotomies remove less tissue than the laminectomy, resulting in less scaring, vertebral instability and blood loss.

Multiple laminotomies, however, also suffer from problems and disadvantages. Laminotomies may not adequately relieve nerve compression and the pain may continue. Laminotomies are more difficult to correctly perform than the laminectomy. Laminotomies expose the nerves and may cause nerve scaring. Patients receiving multiple laminotomies also often have recurrent spinal stenosis requiring risky revision surgery.

For the foregoing reasons, there is a need for different and better methods for relieving the symptoms of spinal stenosis without the drawbacks of currently available techniques. A method is needed that expands the spinal canal, relieving pressure on the spinal nerves, while being simple, safe and permanent.

An initial invention was submitted by the present inventor entitled, "A Method and Implant for Expanding the Spinal Canal" (now U.S. Pat. No. 6,358,254). In the original application, a novel technique was disclosed to expand the spinal canal by lengthening the spinal pedicles on both sides of a vertebra resulting in decompression of compressed nerves while maintaining normal anatomic structures and muscle attachments. This disclosure relies on the same principle, namely that lengthening spinal pedicles can relieve the symptoms of spinal stenosis. This disclosure achieves expansion of the spinal canal by a percutaneous technique, thus eliminating the need for a larger incision.

SUMMARY OF THE INVENTION

The present invention provides a simple, safe, permanent, and minimally invasive method and apparatus for treating spinal stenosis by expanding the spinal canal area to provide additional space for the spinal nerves, relieving pressure on the spinal nerves.

Embodiments of the present invention will be seen variously:

to maintain the integrity of the spinal canal so that the function of normal tissues is not destroyed or significantly altered, which can occur with a laminectomy or laminotomy;

to avoid scarring around spinal nerves by avoiding an open exposure of the nerves;

to avoid an alternative procedure that can cause spinal instability, which occurs when one vertebra slips forward on another vertebra causing recurrent pain and deformity;

to decompress the spinal nerves with a quick, safe approach resulting in minimal blood loss;

to provide a permanent solution to spinal stenosis, where no tendency exists for recurrence; and to achieve decompression of the spinal canal through small percutaneous incisions, rather than a larger incision.

In one aspect of the present invention, a method for correcting spinal stenosis is introduced where a spinal canal is enlarged by cutting a vertebra through one or both pedicles, separating the vertebral cut and then stabilizing the cut. The vertebra can heal with the spinal canal expanded, thereby permanently creating more space for the spinal nerves, and relieving compression on the nerves.

In another aspect of the present invention, the method of expanding the spinal canal includes drilling a passage or hollow tunnel into at least a portion of one or both pedicles of a vertebra, making a pedicle cut (osteotomy) from within the passage through to the spinal canal and to the outside of the vertebra, distracting the osteotomy to lengthen the pedicle, thereby expanding the spinal canal. The osteotomy could then be stabilized. The osteotomy can be distracted by longitudinally lengthening the passage in the pedicle (about the cut) from within the passage. In this aspect, distraction occurs without (and not as a result of) impaction or insertion of a stent or implant into the pedicle cut. Or, in other aspects of the invention, distraction can occur by impaction or insertion of a stent or implant into the osteotomy.

In another aspect of the present invention, the method of expanding the spinal canal includes the following steps: first, a guide wire is inserted into a central portion of the vertebral pedicles on each side of a vertebra. This and other method steps can be accomplished with the assistance of x-rays, fluoroscopy, CAT scan or computer assisted image guidance technology, well known in the art of spinal surgery.

Second, the guide wire is used to direct the position of a cannulated drill (drill with a central barrel or passage to allow introduction over the guide wire) into each of pedicles to form a passage or hollow tunnel in the central portion of each pedicle. At the conclusion of this step the pedicles comprise a hollow column of bone having a central passage and thin, cylindrical, bony walls.

Next, the vertebral pedicles are cut circumferentially, forming an upper portion and a lower portion. A side-cutting instrument can be introduced into the central passage in each pedicle to perform the circumferential cut from within the passage. The side-cutting instrument has a cutting surface that projects radially outward so that the bony walls of each pedicle can be circumferentially cut. With both pedicles circumferentially cut, the vertebra is divided into an upper portion (including the spinous process, lamina, transverse process and articular processes) and a lower portion (including the vertebral body). The side-cutting instrument could include a rotating cutting burr or osteotome (chisel) as the cutting surface, both of which are well known in the art.

Next, each osteotomy (site of the circumferential bone cut) is distracted (widened or expanded) to lengthen the respective pedicle. A specially designed implant can be used to distract the osteotomy by longitudinally lengthening the passage in the pedicle from within the pedicle. In one aspect of the present invention, the implant can include an outer sleeve and an inner bolt in communication with the outer sleeve. Movement of the inner bolt in relation to the outer sleeve longitudinally lengthens the implant to widen the osteotomy, thereby expanding the spinal canal.

In another aspect of the present invention, the implant can be threadably inserted into the central passage in each pedicle, and can include an outer sleeve divided into an upper and a lower portion. In this or another aspect, movement of the inner bolt in relation to the outer sleeve causes the inner bolt to translate the upper portion away from the lower portion to widen the vertebral cut. Further, the division of the upper and lower portion could be positioned at the site of the bone cut. Accordingly, in this or another aspect, the implant could include an inner bolt capable of drawing the upper and lower portions of the outer sleeve apart, and where each part could respectively attach to the upper or lower portion of the pedicle by exterior threads which grip the bony walls of the pedicle. The inner bolt could communicate in a bearing relationship with the lower portion, or could abut the lower portion.

The lower portion of the outer sleeve could also include expandable flanges which expand by the action of the inner bolt of the implant, resulting in the flanges being positioned between the drawn apart edges of the cut pedicle. The inner bolt of the implant could ultimately span across the separation between and engage the upper and lower portions of the outer sleeve, allowing secure fixation of the upper and lower portions of the outer sleeve by the action of the inner bolt.

Finally, the pedicle cut is secured in the elongated position, which can be accomplished by the action of the expandable flanges interposed between the cut surfaces of the pedicle and the inner bolt, the inner bolt securing the upper and lower portions of the outer sleeve by crossing the junction between the upper and lower portions of the outer sleeve.

The drawing apart of the upper and lower portions of the pedicles on each side of the pedicle cut cause expansion of the spinal canal, through lengthening of the pedicle, thereby achieving pressure relief on the spinal nerves. The implants remains in the elongated pedicles, allowing bony healing of the pedicles, and thus creating permanent expansion of the spinal canal and preventing recurrence of the spinal stenosis.

In another aspect of the present invention, the expandable flanges include osteogenic material to assist in the healing of the osteotomy site, allowing the pedicles to heal in the elongated position, thereby permanently expanding the spinal canal.

In another aspect of the current invention, the implant includes a central barrel allowing introduction of the implant over a guide wire.

The present invention differs from current, unrelated techniques for treating spinal stenosis for at least the following reasons:

(1) Normal spine structures are not removed and thus normal muscle attachments are maintained;

(2) There is less chance of spinal instability;

(3) There is less manipulation of the spinal nerves;

(4) There is less scaring around the spinal nerves;

(5) Spinal decompression is more complete;

(6) The operation is quicker and safer with less blood loss;

(7) The expanded spinal canal is permanent, preventing recurrent spinal stenosis; and (8) The procedure can be accomplished in a percutaneous fashion through very small incisions.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

Figure 1:
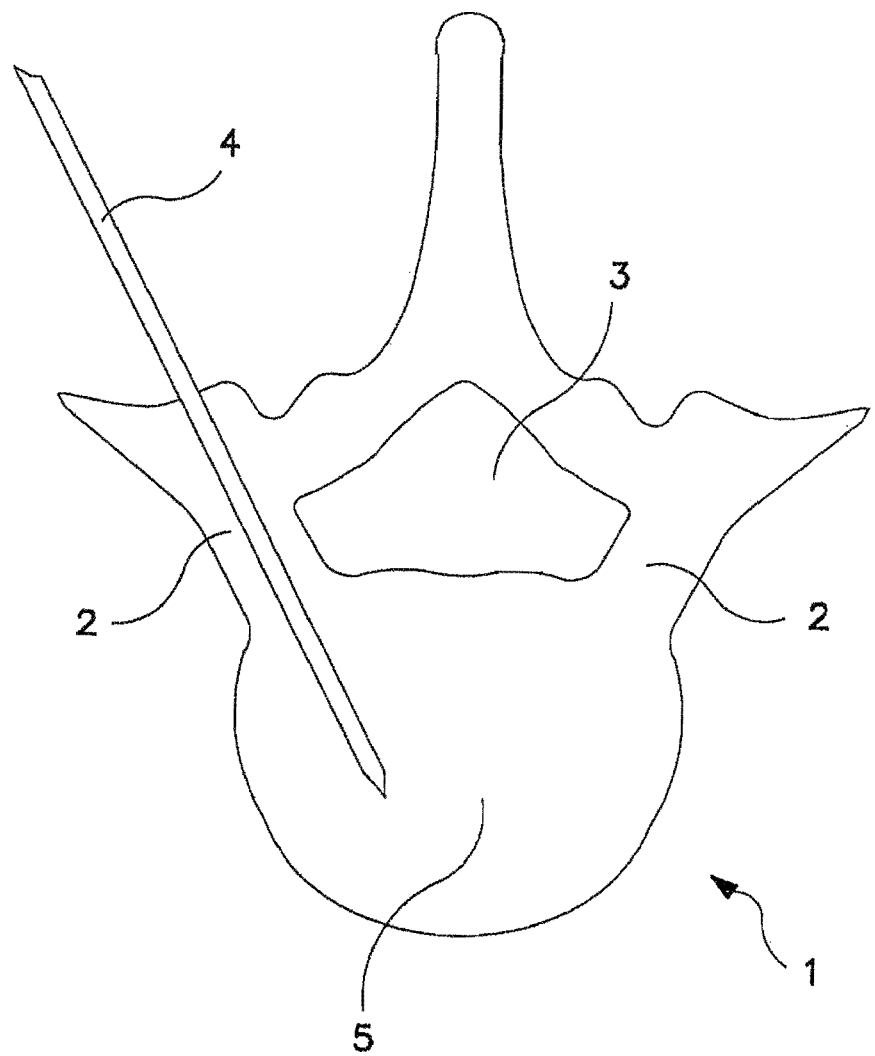
FIG. 1 illustrates a cross-section of a vertebra with a guide wire passing through a central region of a pedicle.

Referring now to the drawings, where like numeral indicate like elements, there is shown in FIG. 1 a cross section of a vertebra 1 having a vertebral body 5, spinal canal 3 and pedicles 2. Also shown is a guide wire 4 inserted into a central portion of the left pedicle 2 to enter the vertebral body 5.

Figure 2:
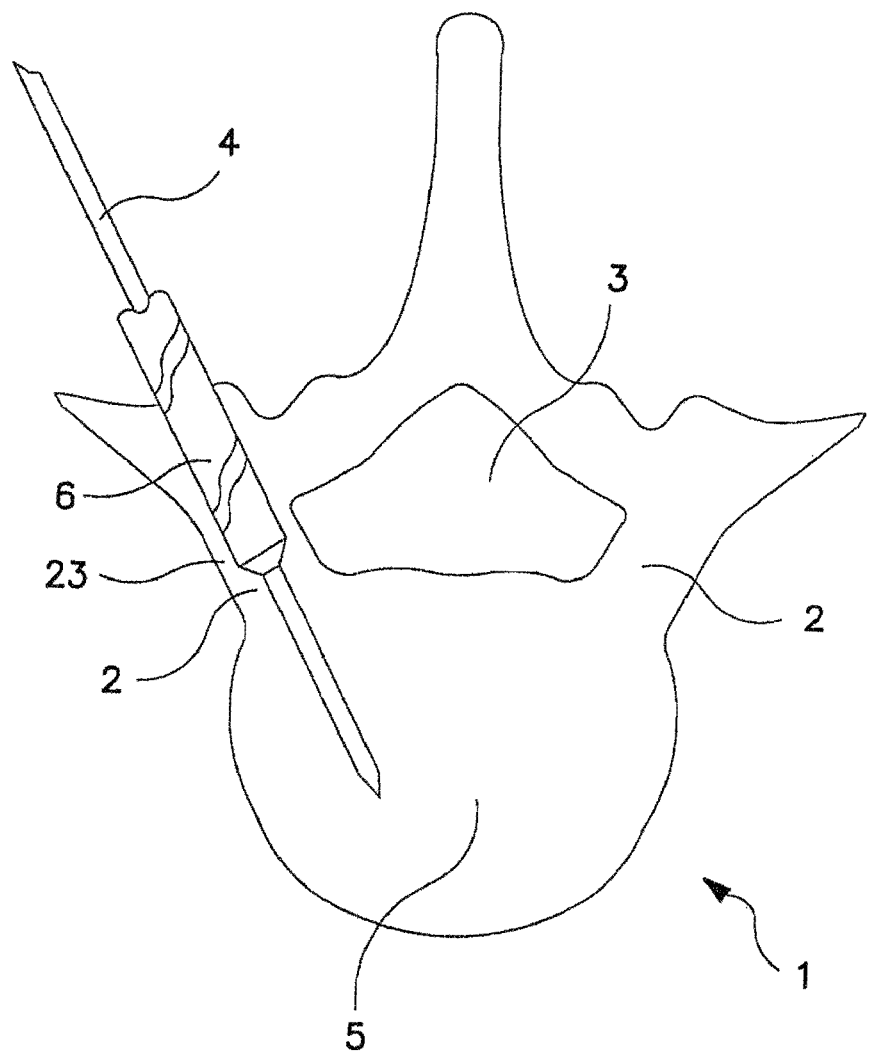
FIG. 2 illustrates the cross-section of the vertebra of FIG. 1, with a cannulated drill passing over the guide wire and drilling a passage into the central region of the pedicle.

FIG. 2 illustrates the cross section of the vertebra 1 of FIG. 1, showing a cannulated drill 6 passing over the guide wire 4, drilling a passage in the central portion of the left pedicle 2 but leaving intact outer wall 23 of the left pedicle 2.

Figure 3:
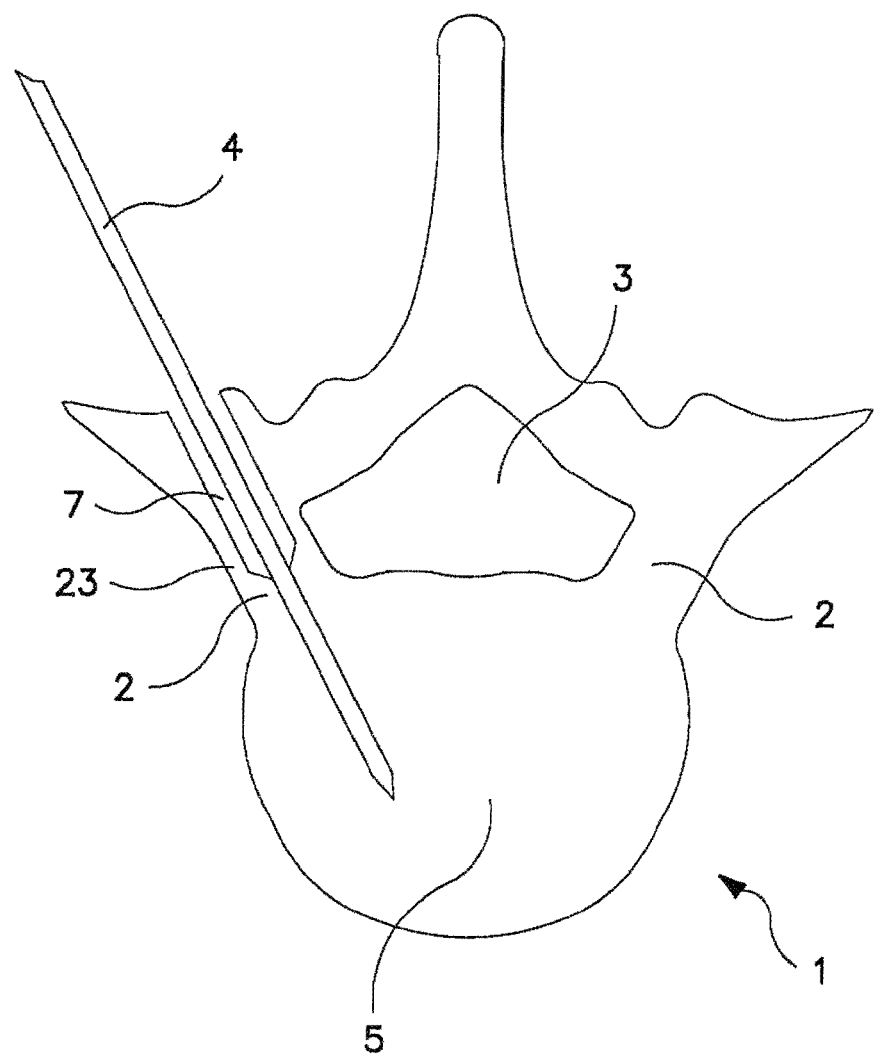
FIG. 3 illustrates the cross-section of the vertebra of FIG. 1, showing a passage (hollow tunnel) in the central region of the pedicle following the cannulated drilling of FIG. 2.

FIG. 3 illustrates the cross section of the vertebra 1 of FIG. 1 following completion of the drilling procedure of FIG. 2, showing a passage 7, or hollow tunnel, spanning the central portion of the left pedicle 2, leaving intact an outer bony wall 23 of the left pedicle 2.

Figure 4:
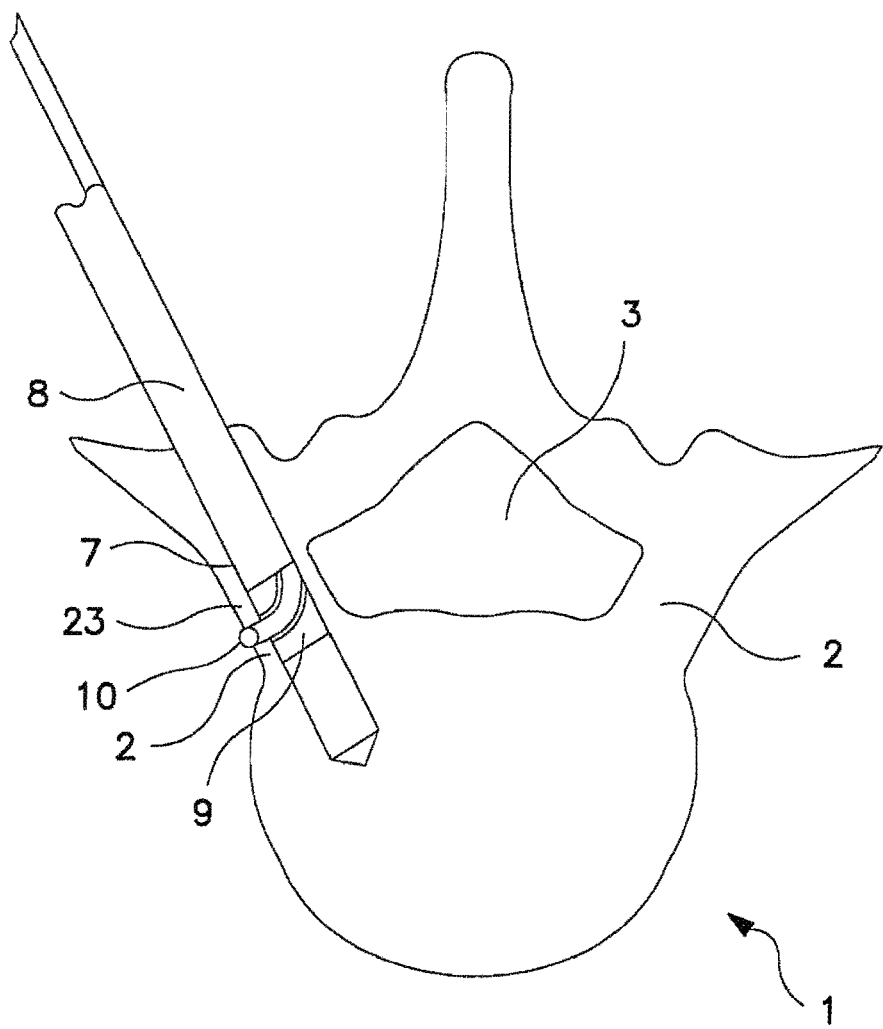
FIG. 4 illustrates the cross-section of the vertebra of FIG. 1, with a side-cutting instrument in the passage in the pedicle performing a cut through an outer bony wall of the pedicle.

FIG. 4 illustrates the cross section of the vertebra 1 of FIG. 1 with a side-cutting instrument 8 within the passage 7 of the left pedicle 2. The side-cutting instrument 8 has an opening 9 which allows a cutting surface 10 to pass radially outward from a longitudinal center of the side-cutting instrument 8. The cutting surface 10 is seen penetrating the outer bony wall 23 of the left pedicle 2.

Figure 5:
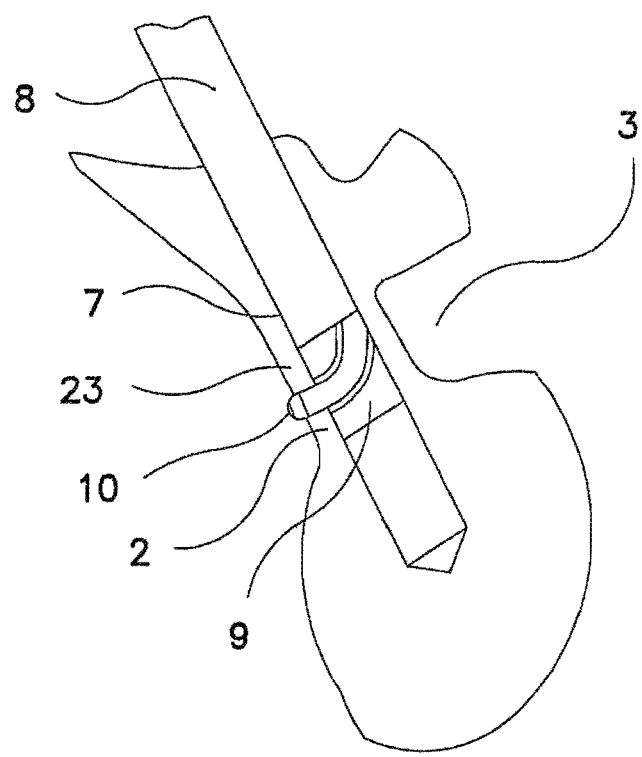
FIG. 5 illustrates an enlarged view of FIG. 4, showing a cutting surface of the side-cutting instrument penetrating through the outer bony wall of the pedicle.

FIG. 5 illustrates an enlarged view of the cross section of the vertebra 1 of FIG. 1, showing the side-cutting instrument 8 within the passage 7 of the left pedicle 2. The cutting surface 10 is passing radially outward from the side-cutting instrument 8 and penetrating the outer wall 23 of the left pedicle 2. The cutting surface 10 of the side-cutting instrument 8 is capable of extending and withdrawing in such a way that it can penetrate through the bony wall 23 of the left pedicle 2. By extending and withdrawing the cutting surface 10, and turning the side-cutting instrument 8 within the passage 7, exposing the opening 9 and the cutting surface 10 to pedicle wall material, the side-cutting instrument 8 can create a circumferential cut (an osteotomy) through the left pedicle 2, separating the left pedicle into two portions, an upper portion and a lower portion.

Figure 6:
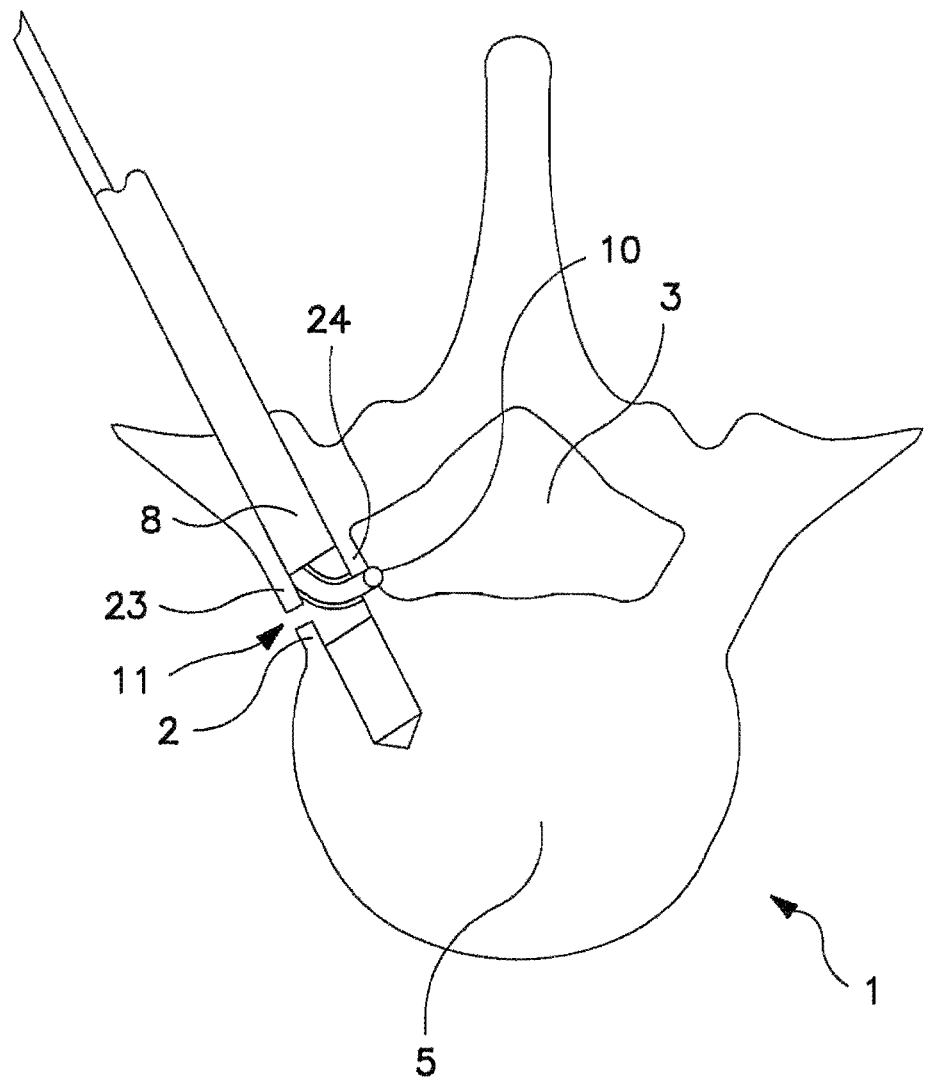
FIG. 6 illustrates the cross-section of the vertebra of FIG. 1, with the cutting surface of the side-cutting instrument completing a cut through an inner bony wall of the pedicle to the spinal canal.

FIG. 6 illustrates a cross-section of the vertebra 1 of FIG. 1 with the cutting surface 10 of the side-cutting instrument 8 extended and penetrating an inner wall 24 (along the spinal canal 3) of the left pedicle 2, creating a cut through to the spinal canal 3.

Figure 7:
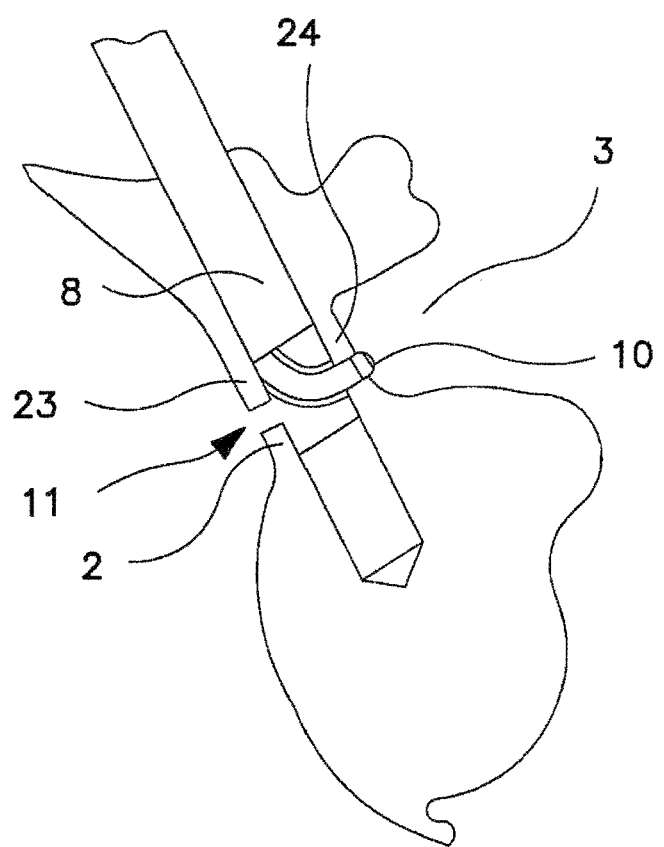
FIG. 7 illustrates an enlarged view of FIG. 6, showing the cutting surface of the side-cutting instrument penetrating through the inner bony wall of the pedicle to the spinal canal.

FIG. 7 illustrates an enlarged view of the cross section of the vertebra 1 of FIG. 1, showing the side-cutting instrument 8 within the passage 7 of the left pedicle 2. The cutting surface 10 is passing radially outward from the side-cutting instrument 8, penetrating the inner bony wall 24 of the left pedicle 2 through to the spinal canal 3.

Figure 8:
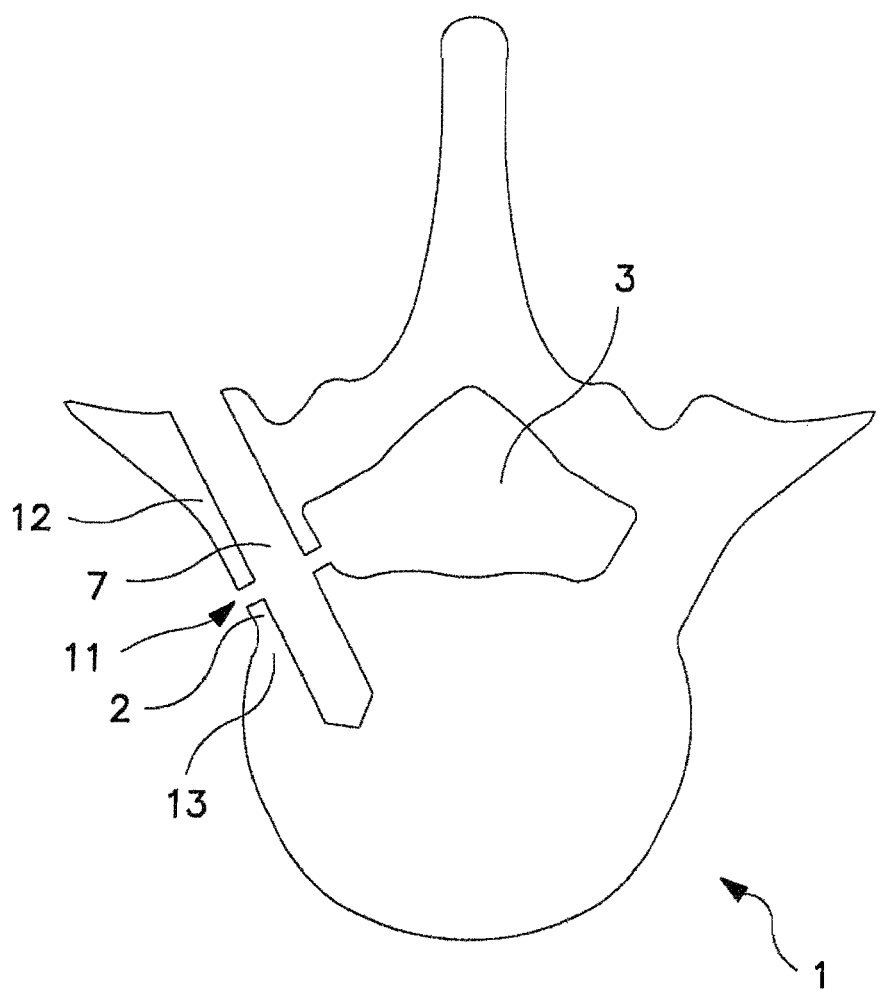
FIG. 8 illustrates the cross-section of the vertebra of FIG. 1, with a completed circumferential cut through the pedicle, separating the pedicle into upper and lower portions.

FIG. 8 illustrates a cross section of the vertebra 1 of FIG. 1 with a completed circumferential cut (an osteotomy) 11 through the left pedicle 2, separating the left pedicle 2 into an upper portion 12 and a lower portion 13.

Figure 9:
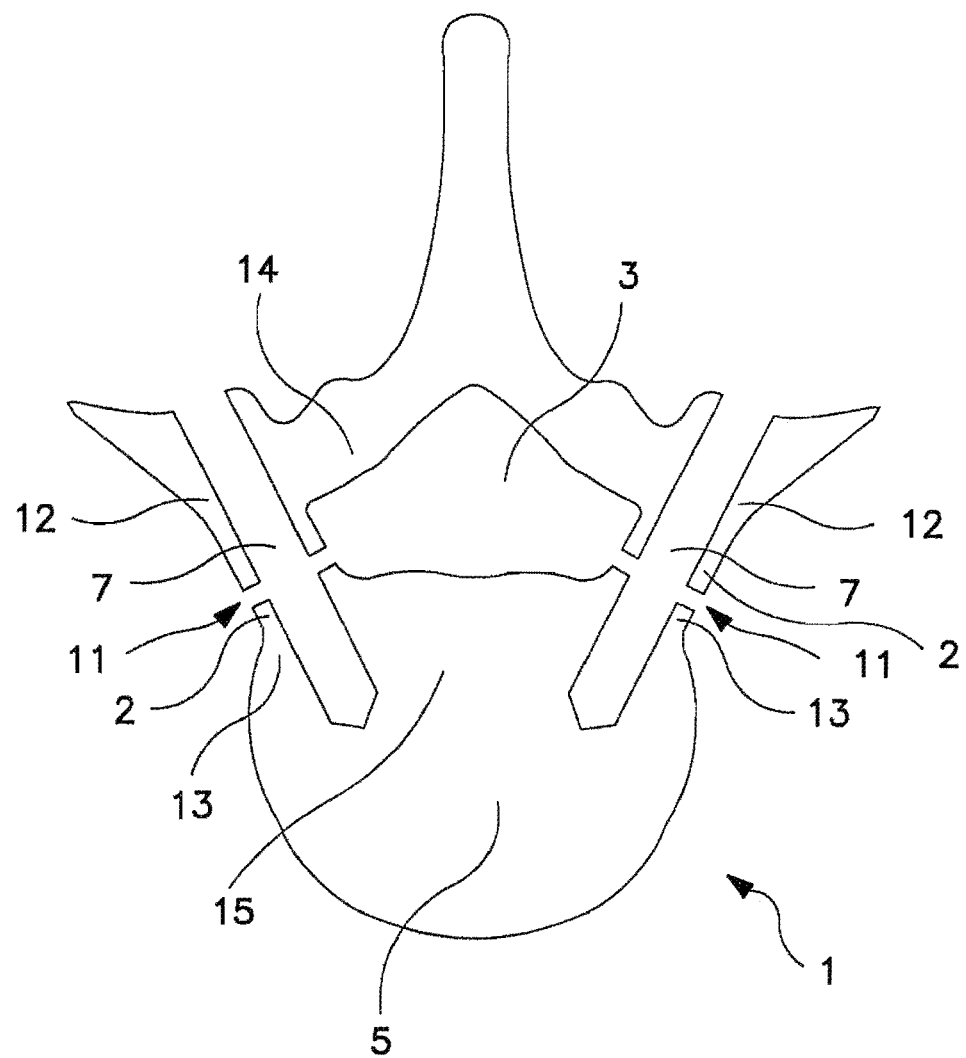
FIG. 9 illustrates the cross-section of the vertebra of FIG. 1, with completed circumferential cuts through both pedicles, separating the vertebra into upper and lower portions.

FIG. 9 illustrates a cross section of the vertebra 1 of FIG. 1, with passages 7 drilled in both the left and right pedicles 2 and circumferential cuts 11 in the midportions of both pedicles 2. The circumferential cuts 11 divide the pedicles 2 into upper portions 12 and lower portions 13 in such a way that upper portion 14 and lower portion 15 of the vertebra 1 are completely detached.

Figure 10:
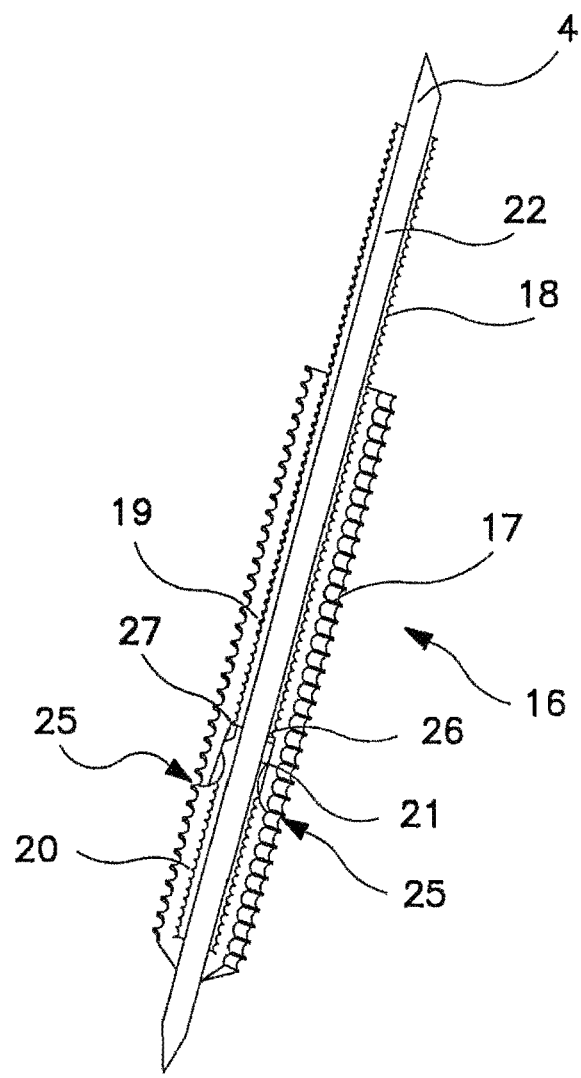
FIG. 10 illustrates a cross-section of an implant used to elongate and stabilize the pedicles, the implant shown in a pre-elongating position.

FIG. 10 illustrates a cross section of an implant 16 used to elongate the pedicles 2, thereby widening the circumferential cut 11 and expanding the spinal canal 3. The implant 16 also secures the pedicles 2 in an elongated position. The implant 16 is shown in a pre-elongating position.

The implant 16 includes an outer sleeve 17 and an inner bolt 18. The outer sleeve 17 is both externally and internally threaded. The inner bolt 18 is externally threaded to engage the internal threads of the outer sleeve 17. The outer sleeve 17 is divided into an upper portion 19 and a lower portion 20. The upper portion 19 and lower portion 20 of the outer sleeve 17 are divided at a separation point 25.

The lower portion 20 contains expandable flanges 21 which fit into the upper portion 19 of the outer sleeve 17 (as shown in FIG. 10) when the implant 16 is in a pre-elongating position. The inner bolt 18 includes a central barrel 22, allowing pass-through of a guide wire 4 (shown in FIG. 10) to assist in correctly aligning the implant 16 within the passage 7 in the pedicle 2. In the pre-elongating position, the inner bolt 18 of the implant 16 is partially housed within the outer sleeve 17. A distal end 26 of the inner bolt 18 contacts the expandable flanges 21 of the lower portion 20 of the outer sleeve 17. The distal end 26 of the inner bolt 18 is designed to not only contact the expandable flanges, but also to wedge itself under a reveal 27 formed due to the flared design of an upper tip of the expandable flanges 21.

Figure 11:
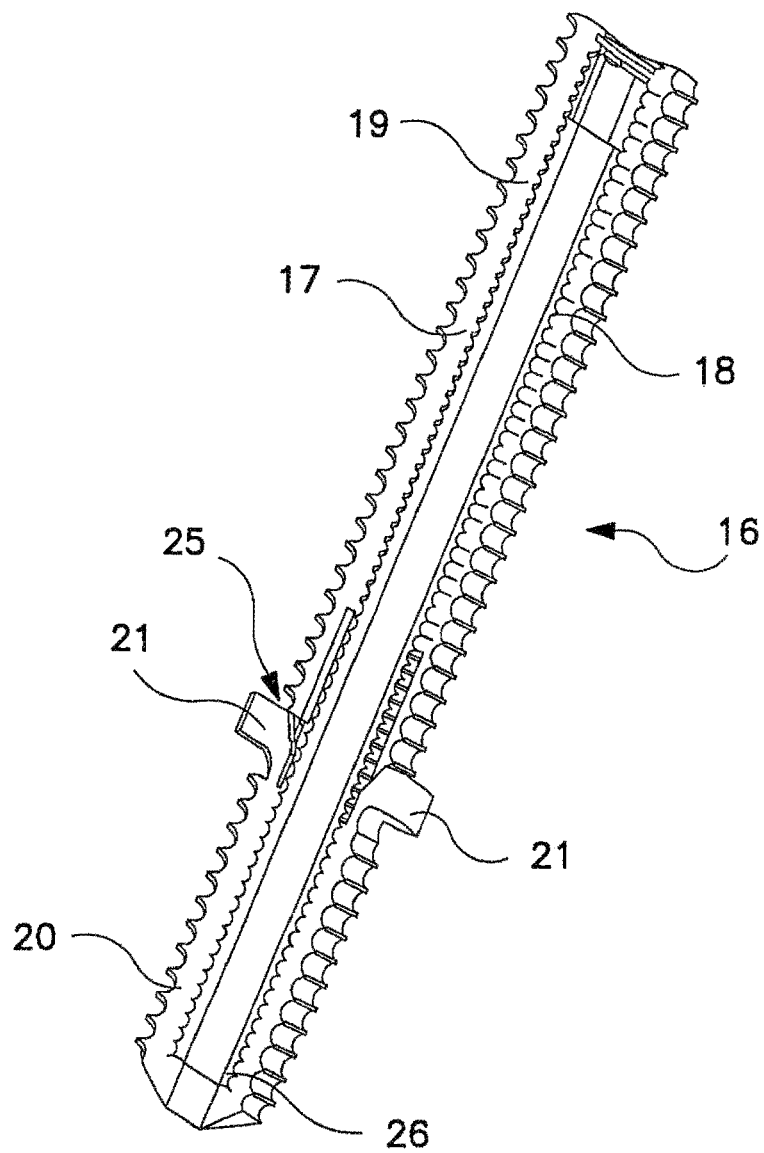
FIG. 11 illustrates a cross-section of the implant of FIG. 10 in a pedicle elongating position.

FIG. 11 illustrates the implant 16 of FIG. 10 in a pedicle elongating position. The inner bolt 18 is fully inserted into the outer sleeve 17. By fully and threadably inserting the inner bolt 18 into the outer sleeve 17, the lower portion 20 of the outer sleeve 17 moves away from the upper portion 19 of the outer sleeve 17, at separation point 25, causing overall elongation of the outer sleeve 17. The expandable flanges 21 of the lower portion 20 of the outer sleeve 17 are opened (expanded) to extend beyond the outer diameter of the outer sleeve 17. In the pedicle elongating position, the expandable flanges 21 lie within the separation between the upper 19 and lower 20 portions of the outer sleeve 17. The upper 19 and lower 20 portions of the outer sleeve 17 are secured in the elongated position by the inner bolt 18, which is threaded across the junction (separation) between the upper 19 and lower 20 portions of the outer sleeve 17, securing the upper 19 and lower 20 portions in the pedicle elongating position.

Figure 12:
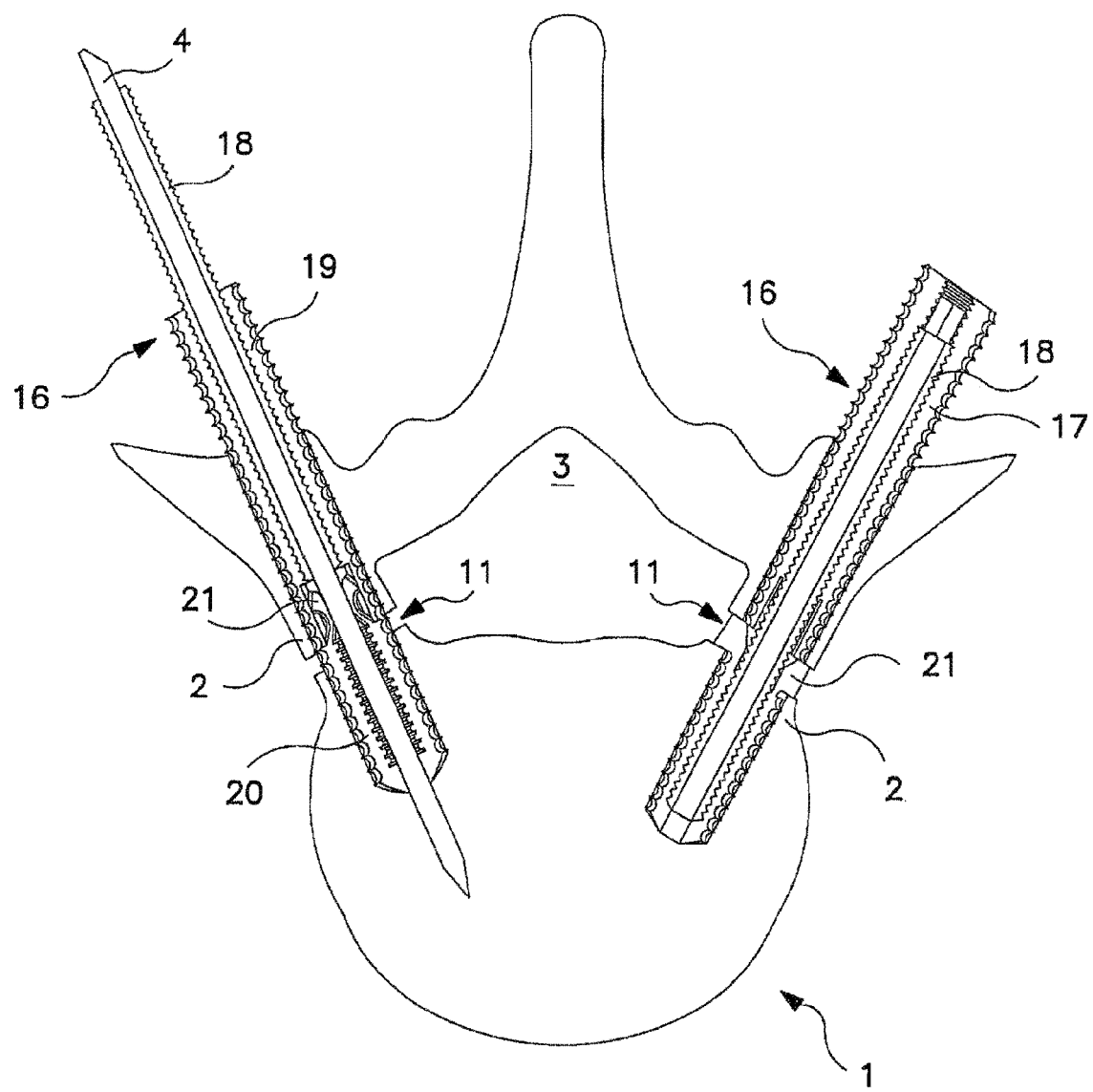
FIG. 12 illustrates the cross-section of the vertebra of FIG. 1, with the implant inserted into the passage of each pedicle, the implant inserted in the left pedicle shown in the pre-elongating position and the implant inserted in the right pedicle shown in the pedicle elongating position.

FIG. 12 illustrates a cross section of the vertebra 1 of FIG. 1, showing the implant 16 inserted into the right and left pedicles 2. The right pedicle 2 includes an implant 16 in a pedicle elongating position, while the left pedicle 2 includes an implant in a pre-elongating position. Note that FIG. 12 shows the right pedicle 2 elongated and the left pedicle in a pre-elongating state. The right, elongated pedicle 2 causes an asymmetrical tilt to the upper portion 14 of the vertebra 1 in the FIG. 12 view, which is balanced upon elongation of the right pedicle 2. Also note the alignment of the separation point 25, in relation to the circumferential cut 11, of the pre-elongated implant 16 in the left pedicle 2.

Figure 13:
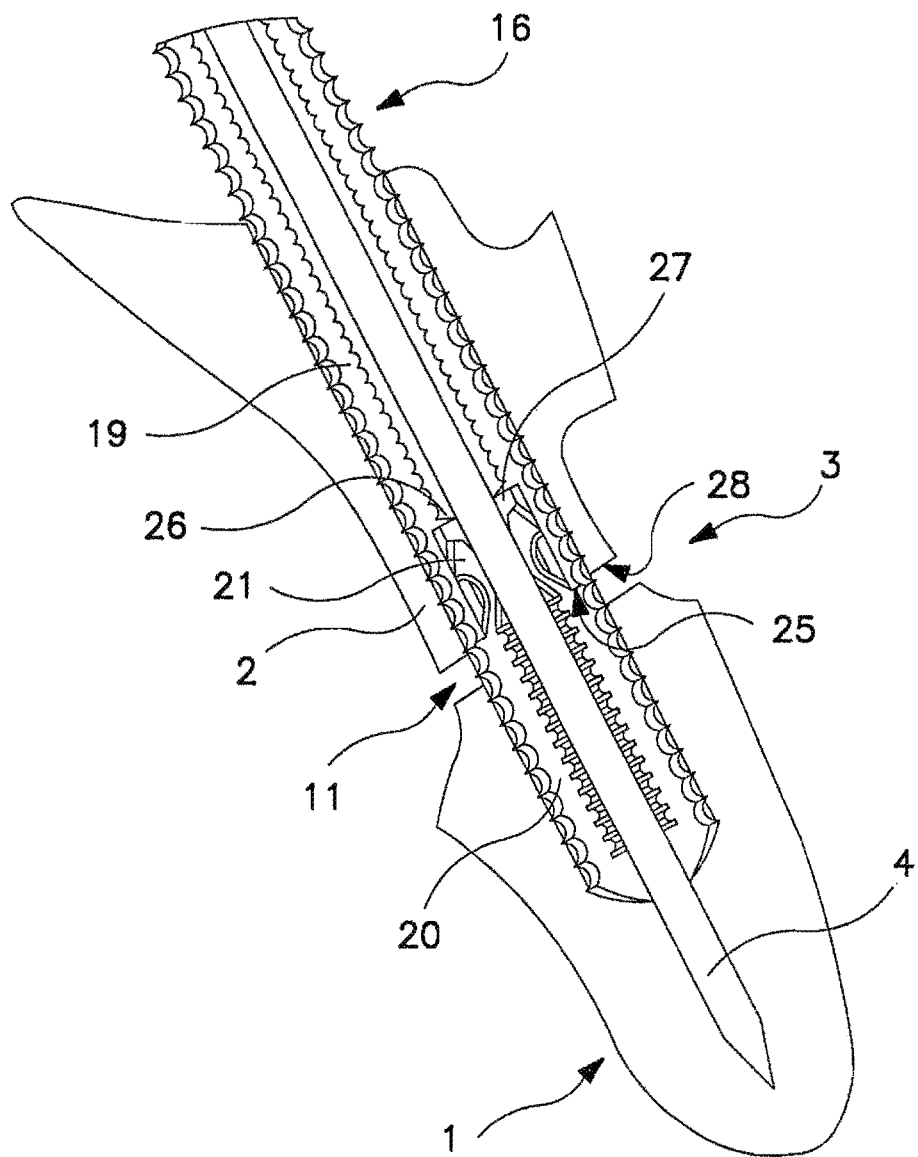
FIG. 13 illustrates an enlarged view of the left pedicle of FIG. 12, showing the implant inserted in the passage in the pre-elongating position and aligned in the passage to begin pedicle elongation.

FIG. 13 illustrates an enlarged view of the vertebra 1 of FIG. 1, showing the implant 16 of FIG. 12 inserted into the left pedicle 2 in a pre-elongating position. The implant 16 is inserted over the guide wire 4 to ensure correct alignment of the implant 16 within the passage 7. In the pre-elongating position, the expandable flanges 21 are housed within the upper portion 19 of the outer sleeve 17. The distal end 26 of the inner bolt 18 contacts the upper tip of the expandable flanges 21. The separation point 25 is positioned adjacent to an upper edge 28 of the circumferential cut (osteotomy) 11.

Figure 14:
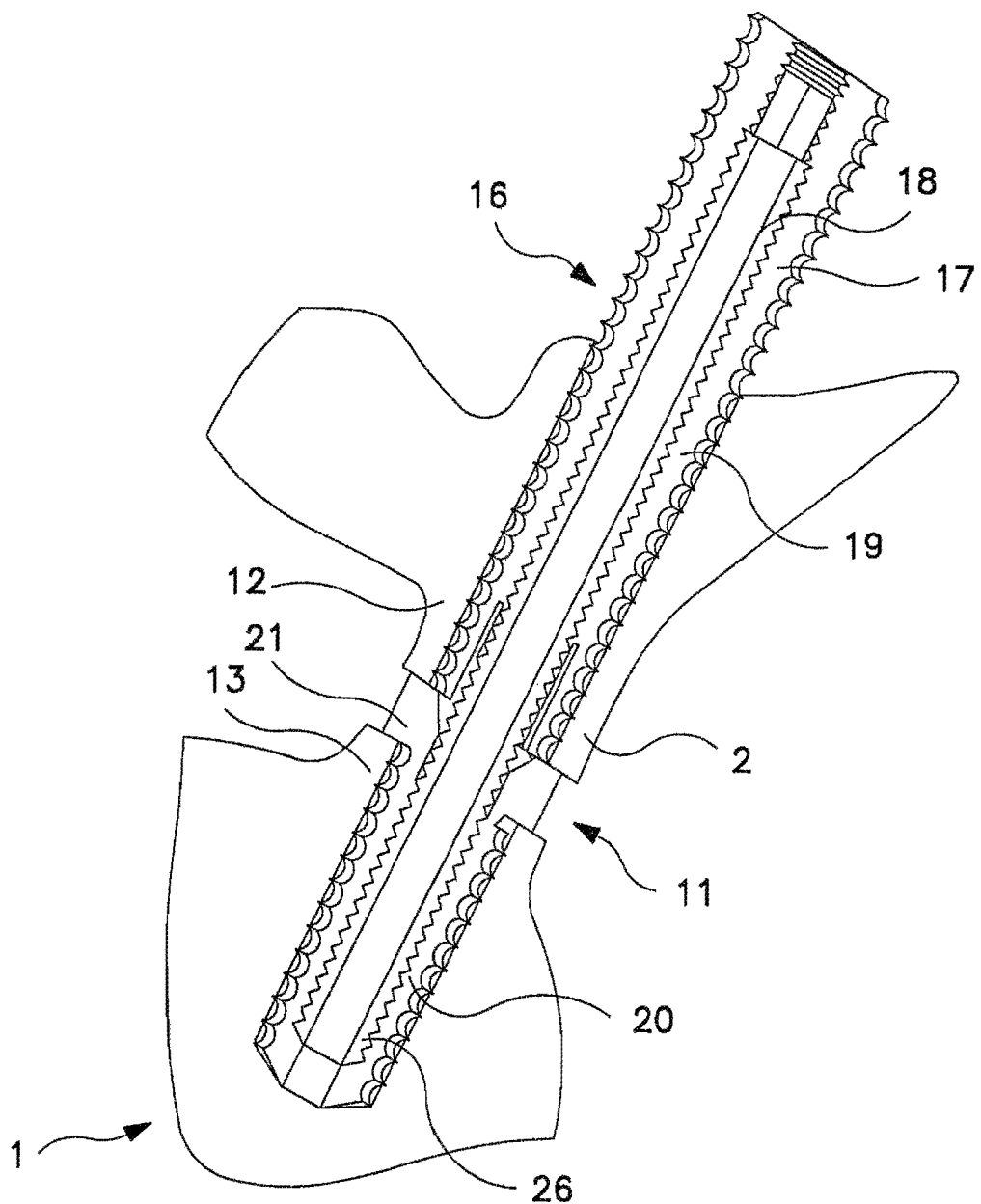
FIG. 14 illustrates an enlarged view of the right pedicle of FIG. 12, showing the implant inserted in the passage in a pedicle elongating position, with expandable flanges of the implant filling and securing a widened circumferential cut in the pedicle after pedicle elongation.

FIG. 14 illustrates an enlarged view of the vertebra 1 of FIG. 1, showing the implant 16 of FIG. 12 inserted into the right pedicle 2 in a pedicle elongating position. The inner bolt 18 has been threadably inserted completely into the outer sleeve 17, causing the upper portion 19 and the lower portion 20 of the outer sleeve 17 to separate, further causing the expandable flanges 21 to open, extending beyond the confines of the outer sleeve 17 and into the circumferential cut 11 of the pedicle 2. The expandable flanges 21, projecting into the circumferential cut 11, prevents the upper portion 12 and the lower portion 13 of the pedicle 2 from moving (shortening) back to their original, non-elongated position.

In operation, one method for expanding the spinal canal is summarized as follows: first, the guide wire 4 is placed into the central portion of the pedicle 2 of the vertebra 1 (FIG. 1). Assistance with the entire procedure (operation) could be obtained through fluoroscopy, x-ray, CAT scan or computerized image guided technology, which are all well known in the art of spinal surgery.

Next, the guide wire 4 is over drilled with a cannulated drill 6, leaving a passage (hollow tunnel) 7 through the central portion of the pedicle 2 but leaving the outer walls 23 intact (FIG. 2). The cannulated drill 6 is then withdrawn, leaving the guide wire 4 in place (FIG. 3).

Next, a circumferential cut (osteotomy) 11 is placed in the pedicle 2 (FIGS. 4-7), using a side-cutting instrument 8 inserted into the passage 7 in the pedicle 2. The side-cutting instrument 8 includes a cutting surface 10, which is extended and withdrawn from a side opening 9 in the side-cutting instrument 8. By extending the cutting surface 10 through the side opening 9 in the side-cutting instrument 8 and turning the side-cutting instrument 8 within the passage 7 of the pedicle 2, the entire pedicle 2 is divided in a circumferential fashion, creating the circumferential cut (osteotomy) 11 (FIG. 8). With both pedicles 2 cut, the upper portion 14 and the lower portion 15 of the vertebra 1 are separated, with no bony material left holding the upper 14 and lower 15 portions together (FIG. 9).

Next, the pedicles 2 are elongated at the site of the circumferential cut 11 using the implant 16 (FIGS. 10-14). The implant 16, in a pre-elongating state, is first threadably inserted into the pedicle 2 using the guide wire 4 to assist the implant 16 into the correct position (left pedicle 2 of FIG. 12). Following insertion of the implant 16, the guide wire 4 is removed.

The pre-elongated extended implant 16 is positioned within the passage 7 of the pedicle 2 to align the upper edge 28 of the circumferential cut 11 with the demarcation (separation) point 25 between the upper 19 and the lower 20 portions of the outer sleeve 17 (FIG. 13). This precise alignment is not critical, however, as placement of the separation point 25 of the outer sleeve 17 within the boundaries of the circumferential cut 11 is sufficient.

The inner bolt 18 of the implant 16 is then threaded into the outer sleeve 17 causing the upper 19 and the lower 20 portions of the outer sleeve 17 to move apart. Because the exterior threads of the upper 19 and the lower 20 portions of the outer sleeve 17 have a good mechanical purchase of the bone of the upper 12 and the lower 13 portions of the pedicle 2, the pedicle is elongated a few millimeters (by a widening of the circumferential cut 11) as the upper 19 and the lower 20 portions of the outer sleeve 17 are drawn apart. The upper portion 19 of the outer sleeve 17 may need to be held motionless to assure that the upper 19 and the lower 20 portions of the outer sleeve 17 begin moving apart.

During rotation of the inner bolt 18, the distal end 26 of the inner bolt 18 pushes against the upper tip of the expandable flanges 21, causing the upper 19 and the lower portions 20 of the outer sleeve 17 to separate until the expandable flanges 21 clear the lower edge of the upper portion 19 of the outer sleeve 17. When the expandable flanges 21 are no longer contained within the upper portion 19 of the outer sleeve 17, the distal end 26 of the inner bolt 18 wedges itself under the reveal 27 (FIGS. 10-11) formed by the upper tip of the expandable flanges 21, pushing the expandable flanges 21 radially outward due to the force exerted by the inner bolt 18. The radial expansion of the expandable flanges 21 allows the inner bolt 18 to travel behind the radially extended expandable flanges 21 and threadably engage the internal threads of the lower portion 20 of the outer sleeve 17 (FIG. 14). The inner bolt is now threadably attached to the upper 19 and the lower 20 portions of the outer sleeve 17, thereby mechanically holding the expandable flanges 21 in an open, radially extended position within the circumferential cut 11, locking the upper 19 and the lower 20 portions of the outer sleeve 17 together, and securing the pedicle 2 in an elongated position (with widened circumferential cut 11) to provide an expanded spinal canal (FIG. 14).

An identical procedure is followed for the pedicles of both the right and the left side of the vertebra 1. To assist with pedicle healing at the circumferential cut 11, the expandable flanges 21 could be made of, or include, an osteogenic material to promote bone healing across the site of the pedicle 2 elongation.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention.

What is claimed is:

1. An implant for expanding a spinal canal, comprising:
   an outer sleeve having an upper portion and a lower portion; and
   an inner bolt in communication with the outer sleeve, wherein movement of the inner bolt in relation to the outer sleeve causes the inner bolt to translate the upper portion away from the lower portion, about a vertebral cut, to widen the vertebral cut and to thereby expand the spinal canal.

2. The implant of claim 1, wherein the vertebral cut is located in a pedicle of a vertebra, and widening the vertebral cut elongates the pedicle, thereby increasing a diameter of the spinal canal.

3. The implant of claim 1, wherein the vertebral cut is located in a lumbar vertebra.

4. The implant of claim 1, wherein the inner bolt is adapted to threadably engage at least a portion of an inner channel of the outer sleeve.

5. The implant of claim 1, wherein the upper portion and the lower portion include external threads to engage a vertebra about each side of the vertebral cut, the upper portion engaging one side of the vertebral cut and the lower portion engaging another side of the vertebral cut.

6. The implant of claim 1, wherein the inner bolt includes external threads that engage internal threads of at least the upper portion.

7. The implant of claim 1, wherein the inner bolt includes external threads capable of engaging internal threads within at least a portion of the upper portion and the lower portion.

8. The implant of claim 1, wherein the inner bolt threadably engages an inner channel of the upper portion to translate the upper portion away from the lower portion about the vertebral cut to widen the vertebral cut.

9. The implant of claim 8, wherein the inner bolt, after threadably engaging the inner channel of the upper portion, bears against the lower portion, to translate the upper portion away from the lower portion about the vertebral cut to widen the vertebral cut.

10. The implant of claim 8, wherein the inner bolt, after threadably engaging the inner channel of the upper portion, communicates in a bearing relationship with the lower portion, to translate the upper portion away from the lower portion about the vertebral cut to widen the vertebral cut.

11. The implant of claim 1, wherein movement of the inner bolt causes an end of the inner bolt to abut the lower portion, separating the upper portion from the lower portion to widen the vertebral cut.

12. The implant of claim 1, wherein the upper portion is mechanically secured to the lower portion after widening of the vertebral cut to maintain the widened vertebral cut.

13. The implant of claim 1, further comprising at least one flange that projects radially from between the upper portion and the lower portion, into the widening vertebral cut, during translation of the upper portion away from the lower portion.

14. The implant of claim 13, wherein the at least one flange secures a width of the widened vertebral cut.

15. The implant of claim 14, wherein the inner bolt secures the upper portion to the lower portion about the at least one flange to maintain the widened vertebral cut.

16. The implant of claim 13, wherein the at least one expandable flange includes osteogenic material to assist with healing of the vertebral cut.

17. The implant of claim 1, further comprising a plurality of expandable flanges housed within the outer sleeve, wherein movement of the inner bolt in relation to the outer sleeve causes the expandable flanges to radially extend outward, beyond an exterior of the outer sleeve, during translation of the upper portion away from the lower portion.

18. The implant of claim 17, wherein the expandable flanges are further housed within the upper portion.

19. The implant of claim 17, wherein the expandable flanges are movably attached to the outer sleeve, wherein movement of the inner bolt causes a distal end of the inner bolt to bear against a respective tip of each expandable flange to radially extend each expandable flange outward beyond an exterior of the outer sleeve and into the vertebral cut, thereby stabilizing the vertebral cut.

20. The implant of claim 19, wherein the inner bolt, after radially extending the expandable flanges into the vertebral cut, mechanically engages the lower portion to positionally secure the upper portion to the lower portion, thereby securing the vertebral cut in a widened position.

* * * * *